(12) United States Patent
Dorrington et al.

(10) Patent No.: US 7,667,847 B2
(45) Date of Patent: Feb. 23, 2010

(54) PHOTOGRAMMETRIC SYSTEM AND METHOD USED IN THE CHARACTERIZATION OF A STRUCTURE

(75) Inventors: Adrian A. Dorrington, Hamilton (NZ); Thomas W. Jones, Smithfield, VA (US); Paul M. Danehy, Newport News, VA (US); Kent A. Watson, New Kent, VA (US); John W. Connell, Yorktown, VA (US); Richard S. Pappa, Newport News, VA (US); W. Keith Belvin, Wicomico, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 85 days.

(21) Appl. No.: 11/533,921

(22) Filed: Sep. 21, 2006

(65) Prior Publication Data
US 2008/0074669 A1   Mar. 27, 2008

(51) Int. Cl.
*G01N 21/55* (2006.01)
(52) U.S. Cl. .................... 356/445; 356/601
(58) Field of Classification Search ......... 356/445–448, 356/601, 614, 620; 382/154, 100, 291
See application file for complete search history.

(56) References Cited

U.S. PATENT DOCUMENTS

| | | | |
|---|---|---|---|
| 5,073,005 A | | 12/1991 | Hubbs |
| 5,440,393 A | * | 8/1995 | Wenz .................... 356/611 |
| 5,446,548 A | * | 8/1995 | Gerig et al. ............. 356/620 |
| 5,855,969 A | | 1/1999 | Robertson |
| 6,587,600 B1 | * | 7/2003 | Shipley .................. 382/284 |
| 6,650,764 B1 | * | 11/2003 | Wakashiro .............. 382/103 |
| 6,852,948 B1 | | 2/2005 | Harrison |
| 6,936,300 B2 | | 8/2005 | Lee et al. |
| 6,936,358 B2 | | 8/2005 | Kume et al. |
| 7,005,603 B2 | | 2/2006 | Addington et al. |
| 7,298,890 B2 | * | 11/2007 | Massen .................. 382/154 |
| 7,369,229 B2 | * | 5/2008 | Bissett et al. ........... 356/328 |
| 7,489,813 B2 | * | 2/2009 | Rutschmann et al. ..... 382/154 |
| 2001/0010392 A1 | | 8/2001 | Corbett |
| 2002/0062077 A1 | * | 5/2002 | Emmenegger et al. ..... 600/443 |
| 2004/0150816 A1 | | 8/2004 | Wakashiro et al. |
| 2005/0000102 A1 | * | 1/2005 | Christoph et al. ........ 33/503 |
| 2005/0100676 A1 | | 5/2005 | Gierow et al. |
| 2007/0153297 A1 | * | 7/2007 | Lau ....................... 356/620 |

\* cited by examiner

*Primary Examiner*—Hoa Q Pham
(74) *Attorney, Agent, or Firm*—Helen M. Galus

(57) ABSTRACT

A photogrammetric system uses an array of spaced-apart targets coupled to a structure. Each target exhibits fluorescence when exposed to a broad beam of illumination. A photogrammetric imaging system located remotely with respect to the structure detects and processes the fluorescence (but not the illumination wavelength) to measure the shape of a structure.

20 Claims, 1 Drawing Sheet

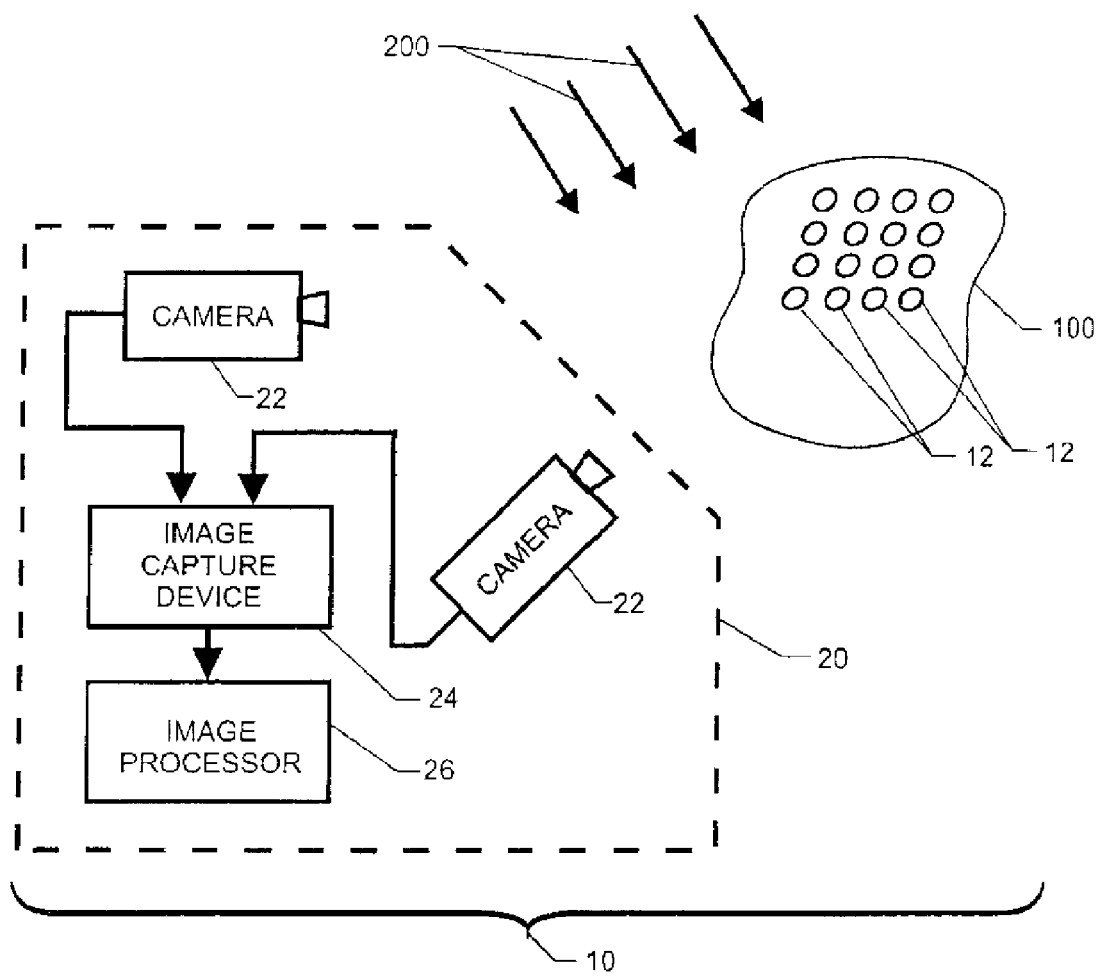
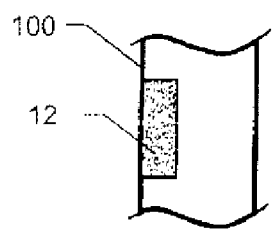
FIG. 2
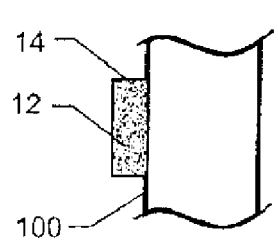
FIG. 3
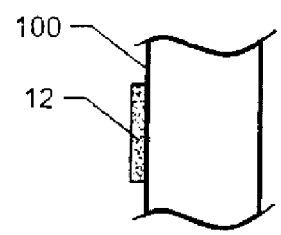
FIG. 4

PHOTOGRAMMETRIC SYSTEM AND METHOD USED IN THE CHARACTERIZATION OF A STRUCTURE

ORIGIN OF THE INVENTION

The invention was made in part by employees of the United States Government and may be manufactured and used by or for the Government of the United States of America for governmental purposes without the payment of any royalties thereon or therefor.

BACKGROUND OF THE INVENTION

1. Field of the Invention

This invention relates to photogrammetry. More specifically, the invention is a photogrammetric system and method used in the characterization of a structure.

2. Description of the Related Art

Photographic images are the result of a perspective projection of a three-dimensional (3D) object onto two dimensions (2D). Consequently, two or more photographic images can be reverse engineered to derive the 3D shape of the original object. This process is called photogrammetry, and the solution provides a quantitative relationship between a 3D object and the 2D images acquired by cameras.

While photogrammetry has its roots in the topographic mapping and surveying field, the last two decades have seen close-range photogrammetric techniques developed to support various industrial and research applications. For example, in some areas of aeronautics aeroelastic experimentation to include model deformation and wing twist, photogrammetric measurements have become part of the standard data set.

Accurate photogrammetric measurements require the photographing of high contrast surface features that appear in at least two images. However, many objects commonly measured do not naturally exhibit such features. Traditionally, retro-reflective targets are attached to the object to artificially provide these high contrast features. When illuminated, these targets reflect light directly back to the illuminating source causing the targets to appear very bright in contrast to the background.

Retro-reflective targets work exceptionally well and have very few drawbacks when used on solid structures. However, retro-reflective targets are not suitable for all types of structures. One example is ultra-lightweight inflatable membrane space structures. The attachment of retro-reflective targets to lightweight membrane structures introduces unacceptable effects such as added stiffness and weight.

An alternative to the attachment of retro-reflective targets is to project target patterns onto a structure. While this non-contact target generation method has advantages with respect to retro-reflective targets, target patterns projected with standard techniques require a diffuse or optically rough surface to work efficiently. However, most membrane-based space structures are made from either highly transparent or highly reflective materials. Target patterns projected onto these types of materials result in the generation of images having poor contrast due to lack of diffusely scattered light and the presence of glints and hot-spot specular reflections from the target-pattern projector.

Laser-induced target generation techniques have been proposed and demonstrated that solve the problems described above, but require the addition of laser dye to the membrane during manufacture. This precludes the use of this these techniques with existing structures that do not already contain the laser dye. For new structures that can be manufactured containing laser dye, this these techniques still requires a laser source and associated optics that complicate the measurement process and introduce eye safety issues. In addition, the size, weight and complexity of the laser source may preclude use of this technique in space applications.

SUMMARY OF THE INVENTION

Accordingly, it is an object of the present invention to provide a photogrammetric system and method for use in characterization of a structure.

Another object of the present invention is to provide a photogrammetric system and method for generating images of reflective or transparent surfaces.

Still another object of the present invention is to provide a photogrammetric system and method that does not require active operation of an illumination source.

Other objects and advantages of the present invention will become more obvious hereinafter in the specification and drawings.

In accordance with the present invention, a photogrammetric system and method are provided for use in the characterization of a structure. An array of spaced-apart targets is adapted to be coupled to a structure. Each target exhibits fluorescence when exposed to a broad beam of illumination. A photogrammetric imaging system located remotely with respect to the structure detects and processes the fluorescence, upon the targets being coupled to the structure.

BRIEF DESCRIPTION OF THE DRAWINGS

FIG. 1 is a schematic diagram of a photogrammetric system in accordance with the present invention;

FIG. 2 is a side view of a single target impregnated in a structure;

FIG. 3 is a side view of a single target impregnated in a polymer material that is affixed to the surface of a structure; and FIG. 4 is a side view of a single target stamped directly onto the surface of a structure.

DETAILED DESCRIPTION OF THE INVENTION

Referring now to the drawings and more particularly to FIG. 1, a photogrammetric system for use in the photogrammetric characterization of a structure is shown and is referenced generally by numeral 10. For ease of illustration, only a portion of the structure is shown and is referenced by numeral 100. By way of illustrative example, structure 100 can be an inflatable structure (e.g., a space structure) made from a reflective or transparent flexible membrane material, a variety of which are known in the art. However, it is to be understood that the inventive aspects of the present invention are not limited by the nature of structure 100 or the material used to construct same. For example, the present invention can also be used in the photogrammetric characterization of rigid structures without departing from the scope thereof.

Photogrammetric system 10 uses a plurality of targets 12 that are coupled to structure 100 in one of a variety of ways that will be explained further below. Targets 12 are typically spaced apart from one another and are arranged in a desired array, although other arrangements of targets can also be used, for example, a random array or arrangement could be used. The number of targets used, spacing between the targets, and shape of the array of targets are design choices that do not limit the scope of the present invention.

In general, each of targets 12 is designed to exhibit fluorescence when exposed to some form of a broad beam of illumination indicated by arrows 200. Illumination 200 can originate from a variety of man-made sources (not shown) such as flood lighting produced by lasers, light emitting diodes (LEDs), light bulbs, etc. Illumination 200 can be defined by a broad or narrow band of wavelengths without departing from the scope of the present invention. Indeed, one of the great advantages of the present invention is that illumination 200 can also originate from a natural source such as the sun, i.e., sunlight or solar illumination.

Each of targets 12 can be a fluorescent dye (or other fluorescent or phosphorescent material) coupled to structure 100 in one of several ways. For the best photogrammetric accuracy, each of targets 12 is circular, however other shapes are possible. The coupling of the fluorescent dye to structure 100 can be achieved as shown in FIG. 2 where target 12 can be selectively impregnated into structure 100 at the surface thereof. By way of example, this could be accomplished by placing the dye in a suitable solvent and depositing it on a compatible surface (e.g., a polymer material). Such selective impregnation could be achieved by dropping, spray coating of a masked region of structure 100, ink jet or other printing techniques, etc.

Another approach for the coupling of targets 12 to structure 100 is illustrated in FIG. 3 where the fluorescent dye indicative of target 12 is impregnated in a shaped piece of film 14 where target 12 is indicated by stippling. A sheet of such film could be manufactured with a high concentration of fluorescent dye as described by A. Dorrington et al. in "Laser-Induced Fluorescence Photogrammetry for Dynamic Characterization of Transparent and Aluminized Membrane Structures," American Institute of Aeronautics and Astronautics, 2003-4798, pp. 1-10. Briefly, in the case of reflective or transparent polymer membranes used for inflatable space structures, the film is typically the same polymer material used for the space structure. After the bulk film is impregnated with the fluorescent dye, shaped (e.g., circular) pieces 14 are cut or "punched out" from the bulk film and attached to the surface of structure 100 using, for example, electroelastic attachment techniques, solvent welding techniques, or adhesive bonding techniques. The thin, lightweight nature of the polymer film minimizes the impact of shaped film 14 on structure 100.

Still another way to "couple" targets 12 to structure 100 is illustrated in FIG. 4. Specifically, the fluorescent dye that forms each target 12 is stamped directly onto the surface of structures 100. Depending on the application, the fluorescent dye could be used by itself or mixed into a carrier. For example, if targets 12 are to be immersed in water, the fluorescent dye could be mixed with a petroleum jelly and applied with a stamp.

A variety of commercially-available fluorescing dyes can be used in the present invention and the particular one is not a limitation of the present invention. One such source for fluorescing dyes is Exciton, Dayton, Ohio, accessible online at http://www.exciton.com. Some suitable examples include Rhodamine 590, Rhodamine 640, and LDS 750.

Referring again to FIG. 1, the remainder of photogrammetric system 10 is a conventional photogrammetric imaging system 20. As would be understood by one of ordinary skill in the art, system 20 includes the following:

at least two cameras 22 for generating two-dimensional images of the array of targets 12 when targets 12 are exhibiting fluorescence, an image capture device 24 coupled to cameras 22, and an image processor (software or hardware or both) 26 for processing the two-dimensional images so-captured to derive the three-dimensional shape of structure 100.

The processed image data can further be supplied to an image output device (not shown) and/or transferred to another device/system for further processing without departing from the scope of the present invention. Note that cameras 22 can incorporate spectral filters to select a fluorescing wavelength or range of wavelengths.

The advantages of the present invention are numerous. Existing or newly-constructed reflective or transparent structures can be readily equipped for photogrammetric characterization. Since the method and system of the present invention can be passively activated into fluorescence using solar illumination, the cost, weight and complexity of laser-induced fluorescence is eliminated. Since the various targets are fixed to a structure as opposed to being projected thereon, photogrammetric characterizations will be sensitive to in-plane motion. Another key advantage of this technology is that the excitation wavelength (laser, LED, or the sun) is typically different than the emission wavelength. Thus, a spectral filter on the camera can reject the laser, LED or solar emission wavelength while efficiently collecting the fluorescence or phosphorescence. This means that reflections or glints from the structure or illumination of the structure would be rejected or attenuated while the desired light emitted from the targets is collected and processed. Thus, the signal-to-noise ratio with the present system is much better than can be achieved with a white-light source and detection system.

Although the invention has been described relative to a specific embodiment thereof, there are numerous variations and modifications that will be readily apparent to those skilled in the art in light of the above teachings. For example, a bulk sheet of a polymer film that is to form a structure could be impregnated with a fluorescent dye in a "caged" (i.e., non-activated) state. The caged dye could be selectively activated (e.g., by exposure to ultraviolet light) to form an array of targets that can exhibit fluorescence such that they would function as previously described herein. It is therefore to be understood that, within the scope of the appended claims, the invention may be practiced other than as specifically described.

What is claimed as new and desired to be secured by Letters Patent of the United States is:

1. A photogrammetric method for use in the characterization of a structure, comprising the steps of:

coupling an array of spaced-apart targets to a surface of a flexible membrane structure selected from the group consisting of reflective membranes and trans went membranes, each of said targets being substantially flat and defined by fluorescent dye;

impinging said array of spaced-apart targets with an unconstrained broad beam of illumination wherein said fluorescent dye exhibits fluorescence; and photogrammetrically imaging said fluorescence exhibited by said array of spaced-apart targets, to thereby characterize the structure.

2. A method according to claim 1 wherein each of said spaced-apart targets is circular.

3. A method according to claim 1 wherein said fluorescent dye is impregnated in the surface of the structure.

4. A method according to claim 1 wherein said fluorescent dye is stamped directly onto the surface of the structure.

5. A method according to claim 1 wherein said fluorescent dye is impregnated into a polymer material attached to the surface of the structure.

6. A method according to claim 1 wherein said unconstrained broad beam of illumination is sunlight.

7. A photogrammetric method for use in the characterization of a structure, comprising the steps of:
forming an array of targets by coupling to a surface of a structure a plurality of targets that exhibit one of fluorescence and phosphorescence, after exposure to a beam of illumination, wherein the structure comprises a flexible membrane selected from the group consisting of reflective membranes and transparent membranes;
impinging said array of targets with a beam of unconstrained illumination; and
photogrammetrically imaging said fluorescence or phosphorescence exhibited by said array of targets, to thereby characterize the structure.

8. A method according to claim 7 wherein said array of targets are impregnated in the surface of the structure.

9. A method according to claim 7 wherein said targets comprise one of a fluorescent and phosphorescent dye that is stamped directly onto the surface of the structure.

10. A method according to claim 7 wherein said targets comprise one of a fluorescent or phosphorescent material that is impregnated into a polymer material attached to the surface of the structure.

11. A method according to claim 7 wherein said unconstrained illumination is at least one of man-made illumination and natural illumination.

12. A method according to claim 7 wherein said unconstrained illumination is sunlight.

13. A method according to claim 7 wherein said array is one of a random array and a predetermined array.

14. A photogrammetric system for use in the characterization of a structure, comprising:
an array of targets adapted to be coupled to a surface of a structure for impingement by unconstrained illumination, each of said targets exhibiting fluorescence when exposed to said unconstrained illumination; and
a photogrammetric imaging system located remotely with respect to the structure for detecting and processing said fluorescence exhibited by said array of targets upon said array of targets being coupled to the structure;
wherein the structure comprises a flexible membrane selected from the group consisting of reflective membranes and transparent membranes.

15. A photogrammetric system as in claim 14 wherein each of said targets is spaced-apart from one another and is circular.

16. A photogrammetric system as in claim 14 wherein each of said targets comprises a fluorescent dye.

17. A photogrammetric system as in claim 16 wherein said fluorescent dye is impregnated in the surface of the structure.

18. A photogrammetric system as in claim 16 wherein said fluorescent dye is stamped directly onto the surface of the structure.

19. A photogrammetric system as in claim 16 wherein said fluorescent dye is impregnated into a polymer material attached to the surface of the structure.

20. A photogrammetric system as in claim 16 wherein said fluorescent dye exhibits said fluorescence in the presence of sunlight.

* * * * *